(12) United States Patent
Reddy et al.

(10) Patent No.: US 9,273,010 B2
(45) Date of Patent: Mar. 1, 2016

(54) PROCESS FOR BENDAMUSTINE HYDROCHLORIDE

(75) Inventors: Bandi Parthasaradhi Reddy, Hyderabad (IN); Kura Rathnakar Reddy, Hyderabad (IN); Dasari Muralidhara Reddy, Hyderabad (IN); Bandi Vamsi Krishna, Hyderabad (IN)

(73) Assignee: Hetero Research Foundation (IN)

( * ) Notice: Subject to any disclaimer, the term of this patent is extended or adjusted under 35 U.S.C. 154(b) by 27 days.

(21) Appl. No.: 14/127,425

(22) PCT Filed: May 24, 2012

(86) PCT No.: PCT/IN2012/000367
§ 371 (c)(1),
(2), (4) Date: Jan. 2, 2014

(87) PCT Pub. No.: WO2012/176214
PCT Pub. Date: Dec. 27, 2012

(65) Prior Publication Data
US 2014/0121384 A1     May 1, 2014

(30) Foreign Application Priority Data

Jun. 20, 2011  (IN) .......................... 2071/CHE/2011

(51) Int. Cl.
*C07D 235/16*   (2006.01)
*C07D 513/04*   (2006.01)

(52) U.S. Cl.
CPC ............ *C07D 235/16* (2013.01); *C07D 513/04* (2013.01)

(58) Field of Classification Search
None
See application file for complete search history.

(56) References Cited

U.S. PATENT DOCUMENTS 8,076,366 B2 * 12/2011 Courvoisier et al. ......... 514/394

FOREIGN PATENT DOCUMENTS

| CN | 101691359 A | 4/2010 |
| WO | 2012176214 A2 | 12/2012 |

OTHER PUBLICATIONS

An English translation of Wang et al., CN 101691359 A, Apr. 7, 2010.*
Gao et al.; "Synthesis of Bendamustine"; Chinese Journal of new drugs 2007, vol. 16(23), 1960-63, English Translation only.
Ozegowsju et al; "Amino Acid Antagonists, III"; J. Pract. Chem. 1963, 20, 178-176—English Machine Translation.
International Search Report and Written Opinion; International Application No. PCT/IN12/00367; International Filing Date May 24, 2012; Date of Mailing Jan. 17, 2013; 8 pages.

* cited by examiner

*Primary Examiner* — Laura L. Stockton
(74) *Attorney, Agent, or Firm* — Cantor Colburn LLP

(57) ABSTRACT

The present invention provides a process for the preparation of 1H-benzimidazol-1-methyl-5-N,N-di(2-hydroxyethyl)-2-butanoic acid ethyl ester. The present invention also provides a process for the preparation of bendamustine hydrochloride. The present invention further provides a process for the purification of bendamustine hydrochloride.

3 Claims, No Drawings

PROCESS FOR BENDAMUSTINE HYDROCHLORIDE

CROSS-REFERENCE TO RELATED APPLICATIONS

This application is a 371 of PCT/IN2012/000367 filed on May 24, 2012, which claims the benefit of Indian Patent Application No. 2071/CHE/2011, filed on Jun. 20, 2011, under the provisions of 35 U.S.C. §119 and the International Convention for the protection of Industrial Property, which are incorporated herein by reference.

CROSS-REFERENCE TO RELATED APPLICATIONS

The present application a 371 of Indian Patent Application No. 2071/CHE/2011, filed on Jun. 20, 2011 under the provisions of 35 U.S.C. §119 and the International Convention for the protection of Industrial Property, which are incorporated herein by reference in their entirety.

FIELD OF THE INVENTION

The present invention provides a process for the preparation of 1H-benzimidazol-1-methyl-5-N,N-di-(2-hydroxyethyl) amino-2-butanoic acid ethyl ester. The present invention also provides a process for the preparation of bendamustine hydrochloride. The present invention further provides a process for the purification of bendamustine hydrochloride.

BACKGROUND OF THE INVENTION

Bendamustine hydrochloride, chemically 5-[bis(2-chloroethyl)amino]-1-methyl-1H-benzimidazole-2-butanoic acid hydrochloride and has the structural formula:

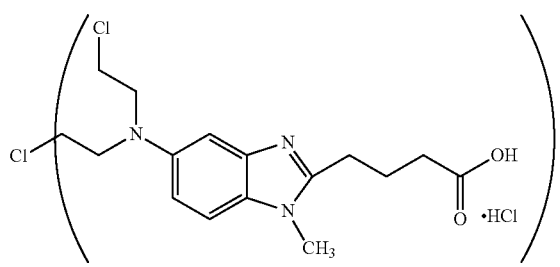

Bendamustine Hydrochloride was initially synthesized in 1963 in the German Democratic Republic (GDR) and was available from 1971 to 1992 there under the tradename Cytostasan®. Since that time, it has been marketed in Germany under the tradename Ribomustin®. Bendamustine hydrochloride is currently available in the United States under the tradename Treanda® (Cephalon, Inc., Frazer, Pa.). Bendamustine is an alkylating agent that has been shown to have therapeutic utility in treating diseases such as chronic lymphocytic leukemia, Hodgkin's disease, non-Hodgkin's lymphoma, multiple myeloma, and breast cancer.

A process for the preparation of 1H-benzimidazol-1-methyl-5-N,N-di-(2-hydroxyethyl) amino-2-butanoic acid ethyl ester was reported in *Journal of pract.chem* 20, 178-186, (1963). According to the journal also reported a process for the preparation of bendamustine hydrochloride.

A process for the preparation of 1H-benzimidazol-1-methyl-5-N,N-di-(2-hydroxyethyl) amino-2-butanoic acid ethyl ester was reported in *Chinese Journal of new drugs* 2007, Vol. 16(23), 1960-63. According to the journal also reported a process for the preparation of bendamustine hydrochloride.

We have found that an improved process for the preparation of 1H-benzimidazol-1-methyl-5-N,N-di-(2-hydroxyethyl) amino-2-butanoic acid ethyl ester.

We have also found that an improved process for the preparation of bendamustine hydrochloride.

4-(7,8-dihydro-6-(2-chloroethylamino)-3-methyl-1,4-thiazino[3,2-g]benzimidazoyl(2))-butyric acid is a potential impurity in bendamustine hydrochloride. The chemical formula of 4-(7,8-dihydro-6-(2-chloroethylamino)-3-methyl-1,4-thiazino[3,2-g]benzimidazoyl(2))-butyric acid may be represented as:

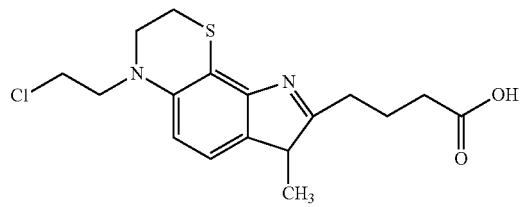 [SMILES: CC1C(CCCC(=O)O)=Nc2c1ccc1c2SCCN1CCCl]

The present invention is intended to enhance the purity of bendamustine hydrochloride. In particular, the present invention is directed to reduce or remove 4-(7,8-dihydro-6-(2-chloroethylamino)-3-methyl-1,4-thiazino[3,2-g]benzimidazoyl(2))-butyric acid impurity from bendamustine hydrochloride.

We have also found that a novel process for purification of bendamustine hydrochloride.

Thus, one object of the present invention is to provide an improved process for the preparation of 1H-benzimidazol-1-methyl-5-N,N-di-(2-hydroxyethyl) amino-2-butanoic acid ethyl ester.

Another object of the present invention is to provide an improved process for the preparation of bendamustine hydrochloride.

Another object of the present invention is to provide a novel process for purification of bendamustine hydrochloride.

SUMMARY OF THE INVENTION

In one aspect, the present invention provides a process for the preparation of 1H-benzimidazol-1-methyl-5-N,N-di-(2-hydroxyethyl) amino-2-butanoic acid ethyl ester, which comprises reacting 1H-benzimidazol-1-methyl-5-amino-2-butanoic acid ethyl ester with ethylene oxide in the presence of an acid characterized in that the quantity of ethylene oxide is 6 to 9 moles with respect to 1H-benzimidazol-1-methyl-5-amino-2-butanoic acid ethyl ester.

In another aspect, the present invention provides a process for the preparation of bendamustine hydrochloride, which comprises:
a) reacting 1H-benzimidazol-1-methyl-5-N,N-di-(2-hydroxyethyl) amino-2-butanoic acid ethyl ester with thionyl chloride in a chlorinated solvent;
b) adding water to the reaction mass;
c) separating the organic layer and discard the water layer;
d) removing the solvent from the organic layer;
e) hydrolyzing ester formed by using hydrochloric acid; and
f) isolating bendamustine hydrochloride.

Yet in another aspect, the present invention provides a process for the purification of bendamustine hydrochloride, which comprises crystallizing from an acidic solution or suspension comprising bendamustine hydrochloride, acetone, water and hydrochloric acid.

DETAILED DESCRIPTION OF THE INVENTION

The term "room temperature" refers to temperature at about 25 to 35° C.

According to one aspect of the present invention, there is provided a process for the preparation of 1H-benzimidazol-1-methyl-5-N,N-di-(2-hydroxyethyl) amino-2-butanoic acid ethyl ester, which comprises reacting 1H-benzimidazol-1-methyl-5-amino-2-butanoic acid ethyl ester with ethylene oxide in the presence of an acid characterized in that the quantity of ethylene oxide is 6 to 9 moles with respect to 1H-benzimidazol-1-methyl-5-amino-2-butanoic acid ethyl ester.

Preferably the moles of ethylene oxide used in the process may be 6.5 to 8 moles with respect to 1H-benzimidazol-1-methyl-5-amino-2-butanoic acid ethyl ester and more preferably the moles of ethylene oxide is 7 to 7.5 moles.

Preferably the acid used in the process is acetic acid.

According to another aspect of the present invention, there is provided a process for the preparation of bendamustine hydrochloride, which comprises:
a) reacting 1H-benzimidazol-1-methyl-5-N,N-di-(2-hydroxyethyl) amino-2-butanoic acid ethyl ester with thionyl chloride in a chlorinated solvent;
b) adding water to the reaction mass;
c) separating the organic layer and discard the water layer;
d) removing the solvent from the organic layer;
e) hydrolyzing ester formed by using hydrochloric acid; and
f) isolating bendamustine hydrochloride.

The chlorinated solvent used in step (a) may preferably be a solvent or mixture of solvents selected from methylene chloride, chloroform, carbon tetrachloride and ethylene dichloride, and more preferably the chlorinated solvent is methylene chloride.

Removal of the solvent in step (d) may be carried out at atmospheric pressure or at reduced pressure. Removal of the solvent may preferably be carried out until the solvent is almost completely distilled off.

Bendamustine hydrochloride may be isolated in step (f) by the methods known such as filtration or centrifugation.

According to another aspect of the present invention, there is provided a process for the purification of bendamustine hydrochloride, which comprises crystallizing from an acidic solution or suspension comprising bendamustine hydrochloride, acetone, water and hydrochloric acid.

The purity of bendamustine hydrochloride was measured by High performance liquid chromatography (HPLC).

The invention will now be further described by the following examples, which are illustrative rather than limiting.

EXAMPLES

Example 1

Preparation of 1H-benzimidazol-1-methyl-5-N,N-di-(2-hydroxyethyl) Amino-2-butanoic Acid Ethyl Ester 1H-Benzimidazol-1-methyl-5-amino-2-butanoic acid ethyl ester (50 gm), water (285 ml) and acetic acid (80 ml) were added at room temperature. The solution was then cooled to 0 to 5° C. under stirring and ethylene oxide gas was passed in the reaction till the reaction mixture weight increases to 60 gm. The reaction mass was maintained for 1 hour at 0 to 5° C. and then temperature allowed to room temperature. The reaction mass was maintained for 30 hours at room temperature and then added water (2000 ml) and dichloromethane (2000 ml). To the reaction mass was added sodium bicarbonate (230 gm) and then the layers were separated. The aqueous layer was extracted with dichloromethane. The organic layers were combined and the solvent was distilled off under vacuum to obtain a residual solid. To the residual solid was added hexane (400 ml) and stirred for 30 minutes at room temperature. The solid obtained was collected by filtration, washed with cyclohexane and then dried at 35 to 40° C. for 2 hours 30 minutes to obtain 63 gm of 1H-benzimidazol-1-methyl-5-N,N-di-(2-hydroxyethyl) amino-2-butanoic acid ethyl ester.

Example 2

Preparation of Bendamustine Hydrochloride

To a solution of 1H-benzimidazol-1-methyl-5-N,N-di-(2-hydroxyethyl) amino-2-butanoic acid ethyl ester (63 gm) as obtained in example 1 in dichloromethane (630 ml) was added thionyl chloride (50.4 gm) for 15 minutes at 0 to 5° C. The contents were heated to 35 to 45° C. and then maintained for 2 hours 30 minutes. To the reaction mixture was added dichloromethane (1000 ml) and then the layers were separated. The aqueous layer was extracted with dichloromethane and combined the organic layers. The organic layer was treated with charcoal (5%, 5 gm) and the solvent was distilled off under vacuum to obtain a residual mass. The residual mass was dissolved in concentrated hydrochloric acid (630 ml) and then heated to 80 to 90° C. The reaction mass was maintained for 3 hours at 80 to 90° C. and the solvent was distilled off under vacuum to obtain a residual solid. To the residual solid was added water (125 ml), stirred for 20 minutes and filtered. The solid obtained was dried to give 54 gm of bendamustine hydrochloride.

Chromatographic purity of bendamustine hydrochloride: 99.2%; and
Content of 4-(7,8-dihydro-6-(2-chloroethylamino)-3-methyl-1,4-thiazino[3,2-g]benzimidazoyl(2))-butyric acid impurity: 0.5%.

Example 3

Purification of Bendamustine Hydrochloride

Bendamustine hydrochloride (54 gm; HPLC Purity: 99.2%) as obtained in example 2 was dissolved in acetone (216 ml) and then heated to 50 to 55° C. To the reaction mixture was added a solution of hydrochloric acid (30 ml of concentrated hydrochloric acid in 270 ml of water) and then added charcoal (5%, 5 gm). The reaction mass was filtered through hi-flow bed and washed with a mixture of acetone and concentrated hydrochloric acid (1:1). The reaction mass was stirred for 45 minutes at 0 to 5° C. and filtered. The solid obtained was washed with water and dried at 35 to 40° C. for 3 hours to obtain 40 gm of substantially pure bendamustine hydrochloride.

Chromatographic purity of bendamustine hydrochloride: 99.88%; and
Content of 4-(7,8-dihydro-6-(2-chloroethylamino)-3-methyl-1,4-thiazino[3,2-g]benzimidazoyl(2))-butyric acid impurity: 0.03%.

We claim:

1. A process for the preparation of 1H-benzimidazol-1-methyl-5-N,N-di-(2-hydroxyethyl) amino-2-butanoic acid ethyl ester, comprising reacting 1H-benzimidazol-1-methyl-5-amino-2-butanoic acid ethyl ester with ethylene oxide in the presence of an acid to form 1H-benzimidazol-1-methyl-5-N,N-di-(2-hydroxyethyl) amino-2-butanoic acid ethyl ester, wherein the amount of ethylene oxide is 6.0 to 7.5 moles with respect to 1H-benzimidazol-1-methyl-5-amino-2-butanoic acid ethyl ester.

2. The process as claimed in claim 1, wherein the amount of ethylene oxide is 7.0 to 7.5 moles with respect to 1H-benzimidazol-1-methyl-5-amino-2-butanoic acid ethyl ester.

3. The process as claimed in claim 1, wherein the acid used in the process is acetic acid.

* * * * *